United States Patent
Suckewer et al.

(10) Patent No.: US 9,351,826 B2
(45) Date of Patent: May 31, 2016

(54) CATARACT REMOVAL USING ULTRA-SHORT PULSE LASERS

(71) Applicants: Szymon Suckewer, Princeton, NJ (US);
Peter Hersh, Far Hills, NJ (US);
Alexander Smits, Princeton, NJ (US);
Richard Register, Princeton, NH (US)

(72) Inventors: Szymon Suckewer, Princeton, NJ (US);
Peter Hersh, Far Hills, NJ (US);
Alexander Smits, Princeton, NJ (US);
Richard Register, Princeton, NH (US)

(*) Notice: Subject to any disclaimer, the term of this patent is extended or adjusted under 35 U.S.C. 154(b) by 240 days.

(21) Appl. No.: 14/269,170

(22) Filed: May 4, 2014

(65) Prior Publication Data
US 2015/0290030 A1   Oct. 15, 2015

Related U.S. Application Data

(60) Provisional application No. 61/978,942, filed on Apr. 13, 2014.

(51) Int. Cl.
*A61B 18/20* (2006.01)
*A61F 2/16* (2006.01)
*A61F 9/008* (2006.01)

(52) U.S. Cl.
CPC ............ *A61F 2/1613* (2013.01); *A61F 9/00834* (2013.01); *A61F 2009/0087* (2013.01); *A61F 2009/0088* (2013.01); *A61F 2009/00887* (2013.01)

(58) Field of Classification Search
USPC ........................................................ 606/4, 5
See application file for complete search history.

(56) References Cited

U.S. PATENT DOCUMENTS

| | | | |
|---|---|---|---|
| 4,538,608 A | 9/1985 | L'Esperance, Jr. | |
| 4,907,586 A * | 3/1990 | Bille | A61F 9/008 606/5 |
| 5,246,435 A | 9/1993 | Bille et al. | |
| 5,656,186 A | 8/1997 | Mourou et al. | |
| 5,993,436 A | 11/1999 | Kitou et al. | |
| 6,099,522 A * | 8/2000 | Knopp | B23K 26/04 606/10 |
| 6,110,116 A | 8/2000 | Wright et al. | |
| 6,146,375 A | 11/2000 | Juhasz et al. | |
| 8,187,256 B2 | 5/2012 | Smits et al. | |
| 8,382,744 B2 | 2/2013 | Suckewer et al. | |
| 8,596,281 B2 | 12/2013 | Suckewer et al. | |
| 2002/0103478 A1 * | 8/2002 | Gwon | A61F 9/008 606/4 |

* cited by examiner

*Primary Examiner* — William Thomson
*Assistant Examiner* — Jeffrey Lipitz
(74) *Attorney, Agent, or Firm* — r.r (princeton); Roy Rosser

(57) ABSTRACT

A system and method of replacing a lens to treat a cataract is disclosed. Cataractous tissue is ablated via a multi-photon process using focused, ultra-short laser pulses. Multi-photon ablation requires an energy intensity between $10^{13}$ to $10^{15}$ W/cm$^2$. Using lasers having femto-second duration pulses, this intensity is achieved with 50 micro-Joules of energy, allowing material disruption with very little heating or shock. The multi-photon ablated material is removed through a micro-channel that leads from the multi-photon ablated region to at least the surface of the eye. Once the material is removed a pre-polymer fluid is injected in to fill the void. This polymerizes into a gel once inside the lens. The polymerized, transformed material matches both the transparency to visible light and the Young's modulus of healthy lens.

18 Claims, 3 Drawing Sheets

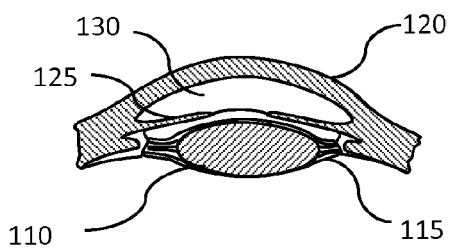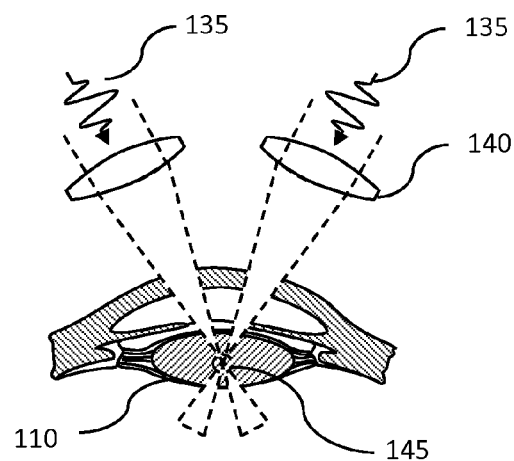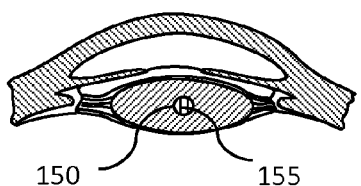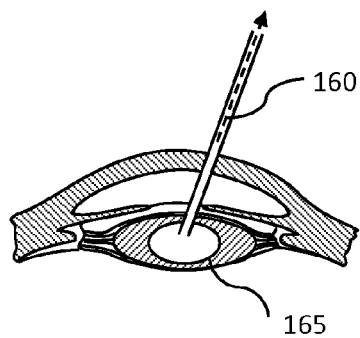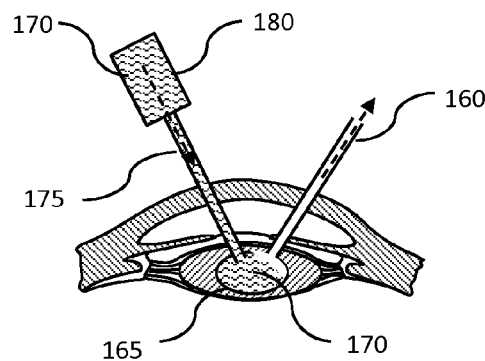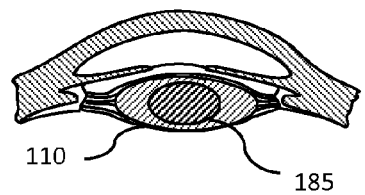
FIG. 1 A
FIG. 1 B
FIG. 1 C
FIG. 1 D
FIG. 1 E
FIG. 1 F

CATARACT REMOVAL USING ULTRA-SHORT PULSE LASERS

CLAIM OF PRIORITY

This application claims no priority to any previous US patent application. The application is related to U.S. Pat. No. 8,187,256, issued on May 29, 2012; U.S. Pat. No. 8,382,744 issued on Feb. 26, 2013; and U.S. Pat. No. 8,596,281 issued on Dec. 3, 2013, the contents of all of which are hereby incorporated by reference.

FIELD OF THE INVENTION

The invention relates to a method and an apparatus for use in ophthalmic surgery, and more particularly to a method and apparatus for restoring vision when the eye lens has developed a cataract. The invention entails the removal of all or part of the cataract affected lens and replacing it with a substitute material, preferably a polymer. The removal of the affected material is preferably by multi-photon ablation using an ultra-short pulse laser.

BACKGROUND OF THE INVENTION

A cataract is a cloudy or opaque region in the lens of the eye, which impairs vision due to a decrease in transparency of the eye lens crystalline material. A common treatment is to surgically remove the entire lens and replace it with an artificial lens, typically made of acrylic or other bio-compatible plastic material.

With the development of laser procedures, such as LASIK to help correct vision by reshaping the cornea of an eye, several other new laser eye procedures are being considered that concern photo-ablation of eye tissue.

For instance, U.S. Pat. No. 4,538,608, issued to L'Esperance, Jr. for "Method and Apparatus for Removing Cataractous Lens Tissue by Laser Radiation" teaches how to deliver laser energy into the anterior of the eye lens and scan the laser beam in order to photoablate cataractous tissue. This procedure was further developed by J. Bille (U.S. Pat. No. 5,246,435 "Method for Removing Cataractous Material"), who proposed a procedure of laser energy delivery to separate lamellae in the stroma by focusing a laser beam between lamellae layers and photoablating tissue at the interface between these layers.

These publications discussed using lasers having pulse lengths of several nanosecond duration (1 nsec=$10^{-9}$ sec, a time in which light travels about 1 foot). With such pulse durations, each laser shot creates undesirable side effects, including strong shock waves within the eye, and significant tissue heating. In the late 1980's ultra-short lasers having pulse durations of less than 1 psec, where 1 psec=$10^{-12}$ sec were developed. The total amount of ablation is a function of both power and the amount of energy delivered to the ablation area. The rate of ablation is, however, only a function of power, not energy, so these ultra-short pulses could produce finely controlled ablation while significantly reducing the undesirable side effects. Such laser have, therefore, beenconsidered for use in eye surgery. For example, T. Juhasz et al., U.S. Pat. No. 5,993,438 "Intrastromal photorefractive keratectomy", T. Juhasz, U.S. Pat. No. 6,110,116 "Method for corneal laser surgery", and T. Juhasz et al., U.S. Pat. No. 6,146,375 "Device and method for internal surface sclerostomy" teach using ultrashort (picosecond and femtosecond) laser pulses for more precisely cutting the so called "flap," in LASIK surgery; employing a photodisruption technique for reshaping the cornea; and for using transcleral photodisruption of tissue on the interior surface of the sclera. Recently, U.S. Pat. No. 7,824,870 granted to Kovalcheck et al. on Nov. 2, 2010 entitled "System for dissociation and removal of proteinaceous tissue" teaches the removal of lens tissue using a high-intensity, electrical ultrashort-pulses between electrodes of the tip of a hollow surgical probe surrounding a volume of lens tissue.

However, in all the above cited patents ultra-short laser pulses, i.e., femtosecond pulses, are used with relatively low intensity, typically less than $10^{-9}$ W/cm$^2$.

In contrast, the present invention uses ultra-short laser pulses of a very high intensity, in range of $10^{13}$-$10^{15}$ W/cm$^2$. This increased intensity significantly alters the nature of the interaction of the pulses with the material. This interaction has become, somewhat erroneously, termed multi-photon ablation to differentiate it from photo-ablation. In traditional photo-ablation, the laser pulse delivers energy that heats the electrons in the material to a sufficient extent to break molecular bonds in the material, freeing the molecules from the material that may, for instance, be the tissue of an eye lens.

In contrast, the process termed multi-photon ablation is a completely different method of material removal than photo-ablation. In multi-photon ablation, individual molecule absorb several photons almost instantaneously, in a time-frame that is faster than the molecule's or atom's relaxation time. This creates an ultra-high electric field in the vicinity of such molecules or atoms that frees them from the tissue being multi-photon ablated. Multi-photon ablation requires a very high laser pulse intensity, equal to or higher than $10^{12}$ W/cm$^2$ and preferably in the range of $10^{13}$-$10^{15}$ W/cm$^2$. This causes a non-thermal ablation of matter, whereas other laser based ablation methods are thermal.

For example, a 5 mJ pulse with 50 femtosecond pulse duration focused down to a diameter of 10 to 100 μm provides a pulse intensity in the range of $10^{13}$-$10^{15}$ W/cm$^2$. At such intensities particles, such as molecules or atoms, at the surface of the target material, for instance tissue, are under a very high electric field, which may exceed the work force, or bonding, of a molecule or atom to the target such as tissue material, therefore freeing them from the target surface and creating the effect of ablation but practically without heating the target material. Initiating multi-photon ablation with a given laser pulse is based on a probability that is most affected by the pulse intensity. So, while multi-photon ablation may be possible below an intensity of $10^{12}$ W/cm$^2$, the probability that a given pulse causes multi-photon ablation at lower intensities is significantly lower, and in practice, negligible. Furthermore, because of the probabilistic nature of multi-photon ablation, descriptions herein of the multi-photon ablation processes do not preclude the possibility that certain laser pulses within such processes may fail to invoke multi-photon ablation and that certain pulses may instead invoke photo-ablation.

In the present invention, the ultra-short laser pulses are directed such that when they reach a focal point within the eye lens, they are focused to such an intensity that at that position they interact with the lens material by the multi-photon processes, and disintegrate cataractous lens tissue by electrical field disruption of the molecular bonds. Such disintegration creates very little heat or shock. Once disintegrated, the lens tissue may be removed partially or fully through a channel formed to access the lens tissue, or by using another instrument such as, but not limited to, a needle or a syringe to evacuate the effluent material. The process has been applied to tattoo removal, cornea reshaping, and presbyopia corrections as detailed in corresponding U.S. Pat. Nos. 8,187,256; 8,382,744; and 8,596,281.

Explanations of multiphoton ablation and related phenomena may be found, for instance in U.S. Pat. No. 5,656,186 "Method for controlling configuration of laser induced breakdown and ablation", issued to G. Mourou et al. the contents of which are incorporated herein in their entirety.

Specifically, Mourou teaches about the relationship between laser fluence threshold for breakdown and photoablation in tissue and laser pulse duration. Fluence (symbol F) is the term used in photochemistry to specify the energy delivered in a given time interval (for instance by a laser pulse) and it is usually measured as the number of Joules deposited per square cm over a certain period of time ($J/cm^2$). Pulse duration is given the symbol $\tau$, and is usually measured in psec. It is shown by Mourou et al. that, starting at a fluence level of F≈10, $J/cm^2$ at a pulse duration $\tau$≈10 nanosecond (nsec), F decreases as $\tau^{1/2}$ over the range from 10 nsec down to 10 picosecond, then decreases by a factor of two for pulse durations from 10 psec down to 1 psec, and then stays constant at F≈0.4 $J/cm^2$ down to 100 fsec.

Therefore, for a pulse duration of $\tau$≈10 nsec, the typical energy (E) required to ablate a surface area of diameter D≈100 micrometer (μm) is E≈1 mJ, whereas with a pulse duration of $\tau$≈100-200 fsec (for such short pulses a typical D≈20 μm) the typical energy required is only E≈1.6 μJ. Hence, to photo-ablate tissue by the multi-photon process using fsec rather than nsec laser pulses, the energy levels required are more than 500 times smaller, and, therefore, shock waves may be negligibly weak for ultra-short pulse laser multi-photo ablation.

Various implementations are known in the art, but fail to address all of the problems solved by the invention described herein. Various embodiments of this invention are illustrated in the accompanying drawings and will be described in more detail herein below.

SUMMARY OF THE INVENTION

An inventive system and method of replacing all or part of a mammalian lens in a mammalian eye is disclosed.

In a preferred embodiment, the portion of the lens required to be removed to treat a cataract may be reduced to a gaseous or liquid form by a process termed multi-photon ablation.

This multi-photon ablated material may then be removed through a micro-channel that leads from the multi-photon ablated region to at least the surface of the eye. Alternately an instrument such as, but not limited to, a needle or a syringe, may be used to evacuate the multiphoton ablated material.

Once the multi-photon ablated material is removed, a transformable material, such as, but not limited to, a pre-polymer fluid may be injected in to fill the void. This fluid may then be transformed into a gel or solid by, a process such as, but not limited to, polymerization.

The transformed material preferably matches, or is a close match, to both the transparency to visible light and the Young's modulus of typical, healthy mammalian lens tissue. The correct transparency may allow the lens to have the appropriate optical properties, and the correct Young's modulus may allow the musculature of the eye to control the lens for functions such as, but not limited to, accomodation, as it is accustomed to doing.

Typically, a material having a Young's modulus in a range of 0.1-20 kPa and a refractive index for visible light in a range of 1.35 to 1.5 may be adequate to function as lens replacement material, though having Young's modulus in a range of 0.5-5 kPa and a refractive index for visible light in a range of 1.38-1.42 may be more desirable.

Multi-photon ablation, the process of disintegration of lens tissue of the preferred embodiment, occurs when the lens tissue is subjected to an intensity of individual laser pulse in a range between $10^{13}$ to $10^{15}$ $W/cm^2$. The enormity of this intensity may be realized by observing that direct sunlight at noon on a clear summer day at the equator provides about 1 $W/cm^2$.

However, by compacting energy, measured in Joules, into a very short time, the power, measured in Joules/sec, aka Watts, can be made large while keeping the actual amount of energy small, and therefore, keeping side effects such as heating and shock low. The intensity, defined as power per area, typically measured in $Watts/cm^2$ can be further increased without additional energy, by concentrating the power in a small volume or area.

The high energy intensity required for multi-photon ablation $-10^{13}$ to $10^{15}$ $W/cm^2$—may, therefore, be achieved by using pulses from a femto- or pico-second laser such as, but not limited to, a Ti-sapphire laser. By focusing a series of ultra-short laser pulses to a focal region within the lens being operated on, if each of said ultra-short pulses has a pulse energy of at least 50 μJ and is focused to spot diameter less than 30 μm, a pulse having the required intensity for multiphoton ablation may be created.

In practice, it may be useful to split the ultra-short laser beam into two or more parts, so that they don't reach a multi-photon ablation threshold before reaching the focal position where material is intended to be removed.

Therefore, the present invention succeeds in conferring the following, and others not mentioned, desirable and useful benefits and objectives.

An objective of the present invention is to provide a method and an apparatus of sufficiently high precision and localization that by cross-focusing two or more laser beams to one point in the tissue, cataractous tissue in the lens may be removed without damaging surrounding or intermediate tissue.

Still another objective of the present invention is to describe a method and an apparatus for the injection of polymer material into the lens capsule of an eye to replace the removed multi-photon ablated cataractous tissue.

BRIEF DESCRIPTION OF THE DRAWINGS

FIG. 1A shows a representation of a horizontal cross-section a portion of a human eye containing the lens.

FIG. 1B shows two ultra-short pulse length lasers focused in a region within a mammalian eye lens in accordance with an embodiment of the method of this invention.

FIG. 1C shows a multi-photon ablated region within an eye lens in accordance with an embodiment of the method of this invention.

FIG. 1D shows a cavity region within an eye lens following removal of multi-photon ablated lens material in accordance with an embodiment of the method of this invention.

FIG. 1E shows a cavity region being filled with a transformable material in accordance with an embodiment of the method of this invention.

FIG. 1F shows a cavity region filled with a transformed material in accordance with an embodiment of the method of this invention.

DESCRIPTION OF THE PREFERRED EMBODIMENTS

Figure 2:
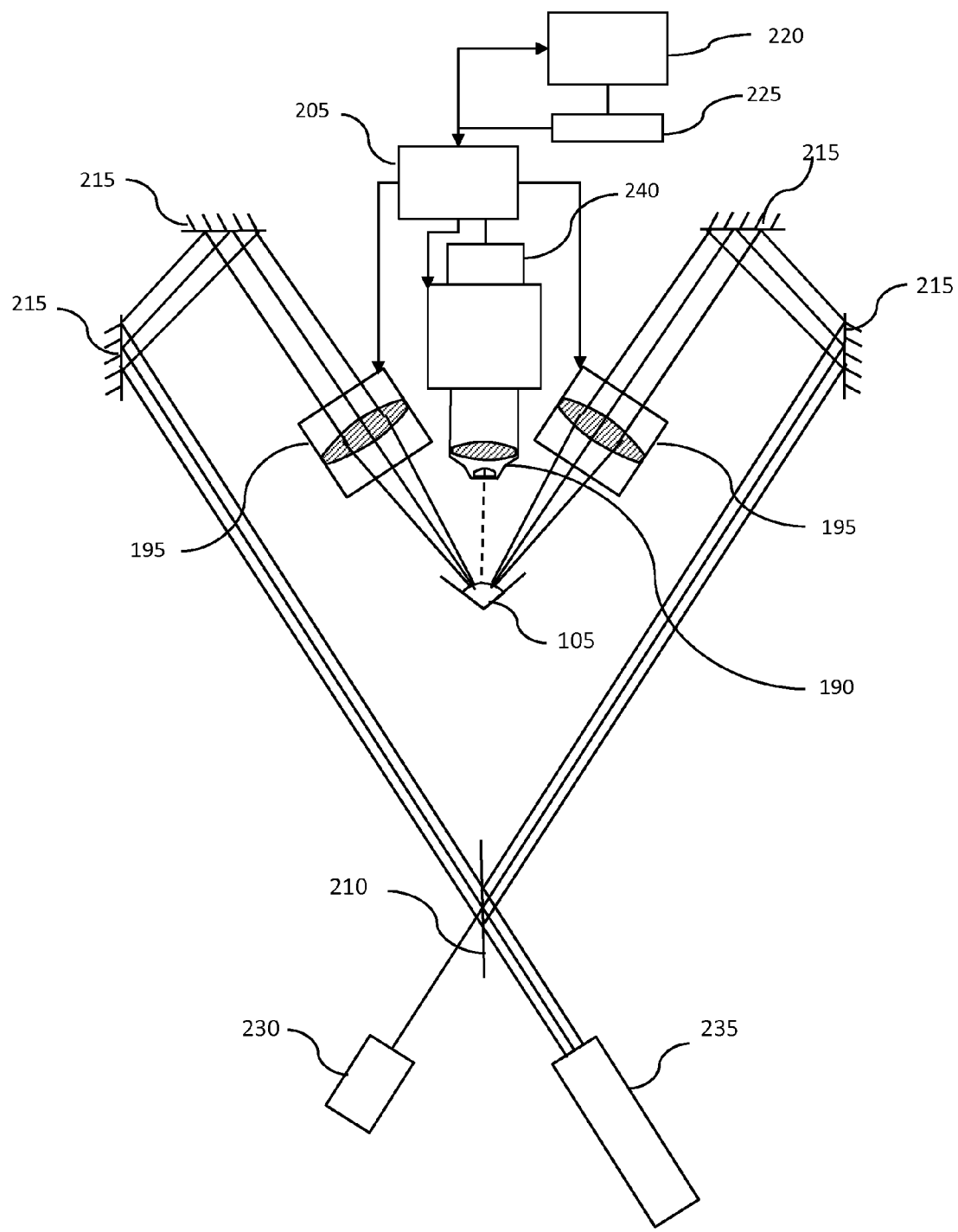
FIG. 2 shows a schematic arrangement of a system for performing an embodiment of the method of this invention.

The present invention is about the method and apparatus for restoring transparency of cataractous tissue in the eye lens or removing cataractous tissue from the lens capsule of an eye and replacing removed multi-photon ablated tissue by polymer material. The method consists of three stages.

In the first stage, a laser beam may be split into N beams (preferable N=2) and cross-focused at the desired point in the lens capsule. For N=2 it is preferable that the entry angle of these two beams into the eye be smaller than 90°, although it is not limited to this angle. For N=1 i.e., a single beam, it is preferable for high precision that the focusing lens has a small f-number such as, but not limited to, f/2 or f/3 in order to localize the focal spot. For N=2 and N>2, the f-number can be larger such as, but not limited to, f/6 and still provide very good localization. Multi-photon ablation of cataractous tissue may then take place, using ultrashort laser pulses i.e., pulses having a duration measured in fsec or psec, and more preferably in a range of about 50-300 fsec. The amount of tissue that is multi-photon ablated may be highly localized, or involve all of the eye lens tissue, or anywhere in between these two extremes. Multi-photon ablation may lead to liquefaction or gasification of cataractous tissue.

In the second stage, a small diameter syringe may be introduced into the region of multi-photon ablation to remove a part or all of the ablated tissue. The syringe is preferably 50 to 200 µm in diameter, although there may be circumstances in which the diameter may be larger or smaller.

If, as a result of the photointeraction of the laser beam(s) with cataractous tissue such tissue becomes transparent to visible light, i.e., the tissue is no longer cataractous, then only a relatively small amount of gas or liquid need be removed so as to restore normal pressure in the eye.

In the third stage, a fluid may be injected through a small diameter syringe to replace the ablated tissue. This fluid, or "pre-polymer", may subsequently be reacted to form a gel, with a comparable index of refraction and tensile modulus to that of the undisturbed crystalline lens. Gel formation within the lens capsule may be produced by a process such as, but not limited to, physical gelation or via chemical reaction, or some combination thereof. The latter route includes, but is not limited to, polymerization and gelation through the reaction of complementary functional groups on components of the pre-polymer mixture; chemically-initiated free-radical polymerization, or photo-polymerization, via a low power laser or flash lamp focused on the injected polymer, or some combination thereof. It is also possible for the pre-polymer to be partially polymerized prior to injection, giving it characteristics intermediate between those of a fluid and a solid.

In a preferred embodiment, the ultrashort laser beam energy may be in range of 50-250 µJ (micro-joule) per pulse with a laser repetition rate that may typically be 10 kHz. Depending on the amount of material being removed, the repetition rate may be lower or higher.

For such ultrashort pulse lasers with pulse durations in the range of 50 fsec up to 10 psec, the total procedure time for ablating a volume of 10 mm³ of cataractous tissue may be in a range of about 5 sec to 20 sec.

The preferred embodiments of the present invention will now be described with reference to the drawings. Identical elements in the various figures are identified with the same reference numerals.

Reference will now be made in detail to embodiments of the present invention. Such embodiments are provided by way of explanation of the present invention, which is not intended to be limited thereto. In fact, those of ordinary skill in the art may appreciate upon reading the present specification and viewing the present drawings that various modifications and variations can be made thereto.

FIG. 1A shows a representation of a horizontal cross-section a portion of a human eye containing the lens.

The section shows a mammalian lens 110 supported by suspensory ligaments 115 behind the iris 125 as well as an anterior chamber filled with aqueous humour 130. The cornea 120 represents the outer surface of the eye, and is the surface exposed to the world and to incoming light. When a cataract occurs, the tissue of the lens becomes less transparent, reducing the amount of light from the outside world that may reach the retina. It is usually a condition of aging, though significant exposure to ultra-violet light may be an accelerating factor. If untreated, a cataract typically progresses to complete blindness in the eye of the infected lens.

FIG. 1B shows two ultra-short pulse length lasers focused in a region within a mammalian eye lens in accordance with an embodiment of the method of this invention.

FIG. 1B represents a first step in the treatment of a cataract in accordance with the method of the present invention. The lens tissue that has become insufficiently transparent must first be removed.

In a preferred embodiment, removal of the insufficiently transparent lens material may be achieved using a process that is currently termed in the art as multi-photon ablation. This may be characterized as a disintegration of the molecular structure of the lens by an extreme intensity, i.e., an intensity in a range of $10^{13}$ to $10^{15}$ W/cm². This degree of intensity may, for instance, be created using a pico- or femto-second laser. In particular, it may be achieved by creating a laser beam pulse having a pulse duration of less than 10 psec, and a pulse energy of at least 50 µJ, and focusing that ultra-short laser pulse down to a focal spot having a diameter less than or equal to 30 µm.

Lasers capable of creating sufficiently short pulse durations, and sufficiently large pulse energies, include lasers such as, but not limited to, the Ti-Sapphire lasers supplied by Thorlabs of Newton, N.J.

Using suitable laser focusing lenses 140, one or more ultra-short laser pulse 135 may be focused down to a sufficient intensity for multi-photon ablation within a focal region 145 within the mammalian lens 110.

With appropriate optics, the focal spot may have an even smaller diameter that may be equal to or less than 10 µm. This may reduce the pulse energy required to achieve multi-photon ablation.

FIG. 1C shows a multi-photon ablated region within an eye lens in accordance with an embodiment of the method of this invention.

The multi-photon ablated region 150 may, for instance, be filled with multi-photon ablated lens tissue 155.

FIG. 1D shows a cavity region within an eye lens following removal of multi-photo ablated lens material in accordance with an embodiment of the method of this invention.

The multi-photon ablated cavity 165 may have been filled with multi-photon ablated of lens tissue. A first micro-channel 160 may be created that may extend from at least the surface of the cornea to the multi-photon ablated cavity 165. This first micro-channel 160 may allow the multi-photon ablated of lens tissue, that may be a liquid or a gas, to exit out of the cavity. The first micro-channel 160 may, for instance, be a gauge 27 or higher hollow needle comprised of a material such as, but not limited to, stainless steel, glass, or a combination thereof. The first micro-channel 160 may alternately be a laser drilled micro-channel as described in, for instance, U.S. Pat. No. 8,382,744 issued to S. Suckewer et al. on Feb. 26, 2013, the contents of which are hereby incorporated by reference.

Alternatively, or in conjunction, a syringe or other suction device, may be attached to the first micro-channel 160 and the multi-photon ablated of lens tissue may be suctioned or vacuumed out.

FIG. 1E shows a cavity region being filled with a transformable material in accordance with an embodiment of the method of this invention.

The transformable material 170 may be injected into the multi-photon ablated cavity 165 via a second micro-channel 175. A syringe 180 that may contain a supply of the transformable material 170 may be attached to the second micro-channel 175 at an end farthest from the multi-photon ablated cavity 165.

The first micro-channel 160 may be in place in order to allow any gas or liquid remaining in the multi-photon ablated cavity 165 to escape and allow the transformable material 170 to enter.

FIG. 1F shows a cavity region filled with a transformed material in accordance with an embodiment of the method of this invention.

The replacement material 185 has been transformed, and now has characteristics that may have the functional physical and optical properties match the properties of a healthy mammalian lens 110.

A preferred material may, for instance, have Young's modulus in a range of 0.1-20 kPa and a refractive index for visible light in a range of 1.35 to 1.5. In a more preferred embodiment, the replacement material may, for instance, have a Young's modulus in a range of 0.5-5 kPa and a refractive index for visible light in a range of 1.38-1.42, so as to more closely match the functional, physical properties of the lens material.

The transformable material discussed above may include a plurality of monomer molecules and the transformation may include polymerization of the monomer molecules into a plurality of polymer molecules. Such a monomer/polymer transformable material may, for instance, further include a catalyst and a polymerization that may occur at a temperature in a vicinity of 98.6 F, so as not to damage surrounding tissue.

One such polymer precursor that may have sufficiently low viscosity to be pumped through a 27 or higher gauge needle, may be a vinyl containing a polyorganosiloxane component, an organosilcon component. Such a material may be polymerized using platinum as a catalyst, and the resulting polymer be a resultant, optically clear, biocompatible polymer.

These materials are described in detail in, for instance, in U.S. Pat. No. 5,278,258 issue to J. Gerace, et al. on Jan. 11, 1994 entitled "Cross-linked silicone polymers, fast curing silicone precursor compositions, and injectable intraocular lenses", the contents of which are hereby incorporated by reference.

Such a composition may, after polymerization, result in an optically clear, cross-linked polymer having a chemical and physical properties suited to use as an intraocular lens.

The polymer may, for instance, be derived from the polymerization of a precursor mixture that may contain a vinyl-containing polyorganosiloxane component, i.e., an organosilicon component that may include silicon-bonded hydride groups that may react with vinyl groups during polymerization.

A catalyst for the polymerization may be an effective amount of a platinum group metal-containing catalyst component.

In a preferred embodiment, the mole ratio of vinyl groups to silicon-bonded hydride groups in the precursor mixture may be at least 6.46 and may, therefore, have a reduced discoloration susceptibility relative to a polymer derived from a substantially similar precursor mixture of ingredients but in which the mole ratio of vinyl groups to silicon-bonded hydride groups in maybe 1.2 or less.

FIG. 2 shows a schematic arrangement of a system for performing an embedment of the method of this invention.

In a preferred embodiment, replacing all or part of a mammalian lens in a mammalian eye 105 may be performed using two lasers, the first being a Femto-second laser 235 that produces the conditions for multi-photon ablation, and the second being a Helium Neon laser 230 that provides a continuous visible laser beam for alignment and monitoring. As shown in FIG. 2, one element of the system or apparatus may be that both lasers follow identical paths after both being split into two beams at beam splitter 210. As shown in the layout of FIG. 2, the two paths followed may be essentially mirrored version of each other, or they may take different geometries that may, for instance, be dependent on the architectural layout of the space in which the equipment is installed. In the layout of FIG. 2, each beam may be steered by two or more minors so as to be aligned along the optical axis of the focusing optical lenses 195. These lenses may be mounted on computer controlled mounts that may allow them to be positioned in three dimensions to at least a sub-millimeter accuracy, and preferably to an accuracy of several micro-meters.

Using the Helium Neon laser 230, the system alignment may be adjusted using an optical microscope 190 that may have an electronic image capture device 240 such as, but not limited to, a CCD array camera that may feed an image to a viewing monitor 220 via an automated control unit 205. The automated control unit 205 may adjust the position of both focusing optical lenses 195 using electronically controlled fine movement controllers such as, but not limited to, precision stepper electric motors, or piezoelectric inch worm drives or some combination thereof.

The automated control unit 205 may also control the position of the optical microscope 190 using similar fine movement controllers, and may also use images obtained from the optical microscope 190 as a feedback look to aid in locating the focal region of each of the lasers at the desired position within the lens of the mammalian eye 105.

This motion control may be effected using prewritten algorithms operative on the automated control unit 205, a feedback loop from the optical images captured by the electronic image capture device 240, or may be done by a user entering commands to the automated control unit 205 via the user input device 225 by a user or care-giver monitoring the eye via the optical microscope 190, or by some combination thereof.

In a preferred embodiment of the present invention, the laser beams may be arranged so that the beams enter the mammalian eye 105 in direction substantially normal to the surface of the eye at the point of entry. This may, for instance, help minimize any aberrations of the beam that may adversely affect the size or quality of the focal spot.

Figure 3:
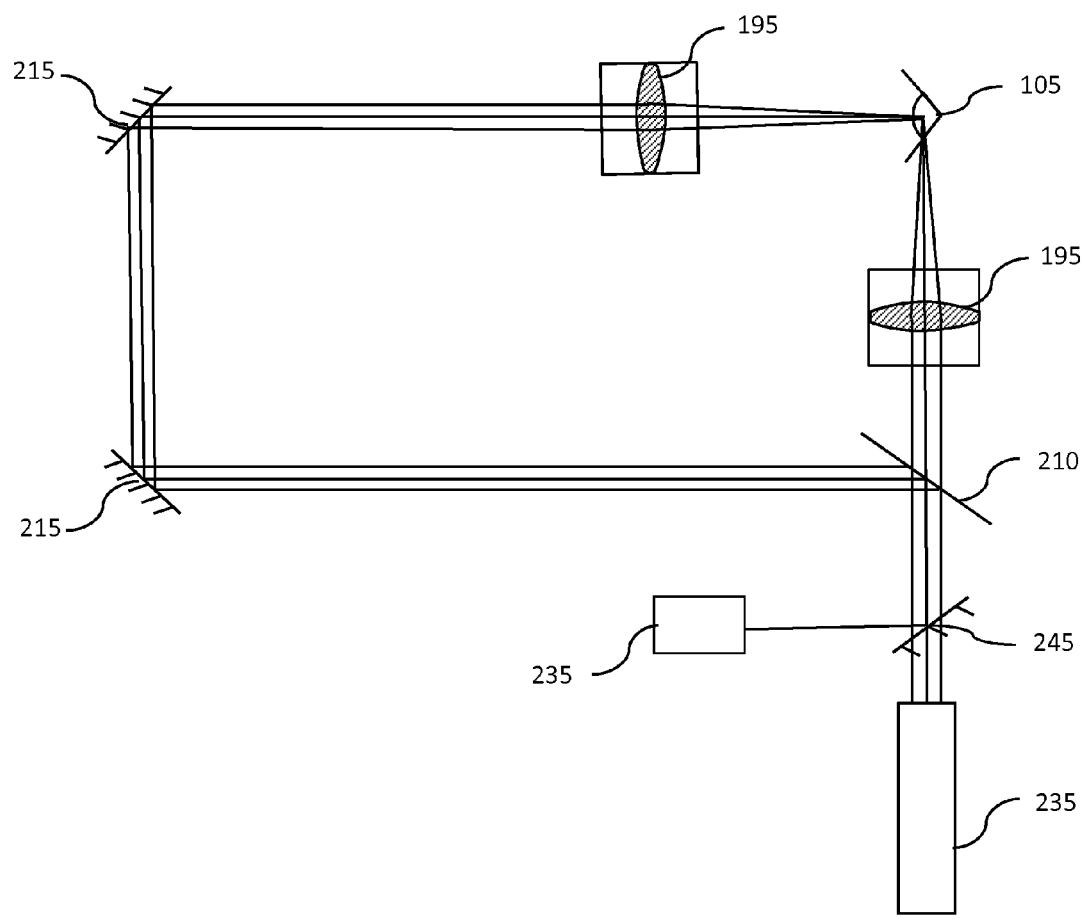
FIG. 3 shows a schematic arrangement of a further embodiment of the optical system for performing this invention.

FIG. 3 shows a schematic arrangement of a further embodiment of the optical system for performing this invention.

In this embodiment there are preferably two ultrashort laser beams that may be tightly focused at a point inside the lens capsule of a patient's eye using lenses 195. The number of laser beams, N, may also be 1 or greater than 2. For the case of N=2, the ultrashort laser 235 beam may be split into two approximately equal intensity beams by beam splitter 210. The preferred ultrashort laser beams are those having a pulse duration τ that may be in a range of 50-300 femtoseconds (fsec). Having τ in a range of 0.5-10 picoseconds (psec) may also be used, but may be less effective.

For N, the number of ultra-short wavelength laser beams, equal to 2, the angle between the two focused beams is typically near 90° or less. The choice of angle may depend on the size and location of cataractous tissue in the lens capsule and is not restricted to 90°. The location of the spot to be irradiated by ultrashort laser pulses may be chosen by using a microscope and HeNe (Helium-Neon) laser beams. These lasers operate in the visible spectrum range at a wavelength λ=632 nm. Other visible light lasers may be used instead, though the HeNe laser 235 is the most wide-spread, commonly used laser for alignment purposes. The HeNe laser beam may be placed on the path of the fsec beam by a special mirror 245, which is transparent for ultrashort laser beams, where the ultrashort beam preferably operates at a wavelength the vicinity of λ=800 nm.

The HeNe beam may be split by a beam splitter 210 into two beams, each of them following the same path as the ultrashort laser beams. However, because they have a different wavelength, the HeNe beams are not tightly focused by focusing optical lenses 195 into the patient's eye. The crossing of HeNe laser beams in the eye may illuminate the lens material. The image may be magnified by an optical microscope and may be shown on a monitor, providing a fast and simple method of choosing cataractous tissue to be multi-photon ablated by the ultrashort laser beams. The focusing optical lens 195 may be moved in the perpendicular (horizontal x-axis) and parallel (z-axis) direction as well as vertical (y-axis) relative to the plane of the beams using a three-stage, remotely controlled, high precision position control system, or micro-scanner. Each scanner may operate one lens and may be computer controlled. The operator may choose the position of the crossing point by observing the microscope images on the monitor and may give instructions to the control system via the computer interface, as illustrated in FIG. 2. The depth of focus of the microscope may, for instance, be controlled either by the computer or manually by an operator. A CCD camera may be used to detect images provided by the microscope, or the eye tissue may be observed directly by the operator using optical eye pieces typically connected to the microscope.

As discussed previously in connection with FIG. 1D, any portion of multi-photon ablated cataractous tissue, either in gaseous or liquid form, may be removed using a hollow needle, or a syringe, having a very small internal diameter, or port. The syringe may, for instance, be inserted into the eye lens and may be connected to a small evacuating pump, or suction mini-pump. The port may be significantly smaller than that used in current cataract surgery procedures, and may be less than 200 μm in diameter. Greater or smaller sizes may however be used to address issues of rate of removal, viscosity of material being removed or some related issue. The syringe may be made of transparent materials such as quartz or non-transparent metal materials such as a stainless steel. Glass may be drawn down to provide very small ports, but stainless steel may provide better durability. Given a total volume of effluent comprising approximately 200 mm$^3$, we may estimate that a flow rate through the port of the order of 0.04 cc/sec may result in a removal/irrigation time of about 5 seconds. Multiple ports may be used to ensure uniform and clean removal of effluent.

A similar syringe may be used for injecting pre-polymer to replace the removed multi photon ablated cataractous tissue. For injection purposes, the mini-pump may, for instance, be operated in reverse to force the pre-polymer into the lens capsule of the eye, as shown schematically in FIG. 1E. In FIG. 1E the tip of the needle may be placed in the lens capsule of the eye in a location where multi-photon ablated cataractous tissue was removed. The injected pre-polymer should preferably be in a liquid state, but it may also be in a gel or a powdered solid state. The pre-polymer needs to be compatible with eye crystalline tissue in terms of index of refraction, transparency, stability and longevity, and should be able to maintain transparency and index of refraction for a large number of years. The pre-polymer and more particularly, the resultant polymer is preferably bio-compatible, i.e., it is preferably benign in terms of its impact on human cells. In another preferred embodiment, the mechanical properties of the polymer may also resemble those of the natural human lens, so that accommodative function may be preserved or restored.

In circumstances in which only a relatively small amount of material may have been multi-photon ablated, it may be possible to avoid using a syringe. This may be particularly applicable when the material remains in the lens in a gaseous state. In such cases, an elongated channel may be created from the surface of the eye to the location of the multi-photon ablated material by using the ultra-short laser pulses. The channel may be up to 5 mm in length and may have a diameter in a range of 20-100 μm. Such a channel may allow the multi-photon ablated material to escape from the eye without further intervention. Such small diameter channels typically heals without further intervention in less than five minutes.

In alternate preferred embodiments, the ultra-short pulses may have a pulse energy in a range of 10-100 μJ and focused to spot diameter in a range of 10-100 μm in order to create a pulse intensity within the focal region in a range of $10^{13}$ to $10^{15}$ W/cm2 or higher. Such intensities may creating a multi-photon ablated region of lens tissue in a vicinity of the focal region.

Although this invention has been described with a certain degree of particularity, it is to be understood that the present disclosure has been made only by way of illustration and that numerous changes in the details of construction and arrangement of parts may be resorted to without departing from the spirit and the scope of the invention.

What is claimed:

1. A method of replacing all or part of a mammalian lens in a mammalian eye, comprising:

focusing a plurality of ultra-short laser pulses to a focal region within said mammalian lens, each of said ultra-short pulses having a pulse energy in a range of 10-100 μJ and focused to spot diameter in a range of 10-100 μm, creating a pulse intensity within said focal region in a range of $10^{13}$ to $10^{15}$ W/cm$^2$, thereby creating a multi-photon ablated region of lens tissue in a vicinity of said focal region;

removing said multi-photon ablated lens tissue from said lens via a first micro-channel extending from a vicinity of said focal region to at least the surface of said mammalian eye thereby creating a multi-photon ablated cavity within said mammalian lens;

injecting a transformable material into said cavity within said lens via a second micro-channel extending from at least said surface of said mammalian eye; and transforming said transformable material, once inside said cavity, to a replacement material having physical and optical properties that substantially match the functional physical and optical properties of a lens of a healthy mammalian eye.

2. The method of claim 1 wherein said replacement material has a Young's modulus in a range of 0.1-20 kPa and a refractive index for visible light in a range of 1.35 to 1.5.

3. The method of claim 2 wherein said transformable material comprises a plurality of monomer molecules and wherein said transformation comprises polymerization of said monomer molecules into a plurality of polymer molecules.

4. The method of claim 3 wherein said transformable material further comprises a catalyst and said polymerization occurs at a temperature in a vicinity of 98.6 F.

5. The method of claim 4 wherein said transformable material comprises a vinyl-containing polyorganosiloxane component, an organosilcon component and wherein said catalyst is a platinum metal containing component, and wherein said replacement material comprises a resultant, optically clear, biocompatible polymer.

6. The method of claim 1 wherein said spot diameter is less than or equal to 10 μm and said replacement material has a Young's modulus in a range of 0.5-5 kPa and a refractive index for visible light in a range of 1.38-1.42.

7. The method of claim 1 wherein said ultra-short laser pulses have a pulse duration of less than 10 psec.

8. The method of claim 7 wherein said ultra-short laser pulses travel toward said focal region along at least two distinct paths.

9. The method of claim 8 wherein said first micro-channel comprises a gauge 27 or higher hollow needle comprised of one of stainless steel or glass, or a combination thereof.

10. The method of claim 9 wherein removing said multi-photon ablated material further comprises functionally attaching a syringe to said hollow needle in a vicinity of an end of said hollow needle furthest from said cavity; and decreasing a pressure within said syringe thereby removing said multi-photon ablated material.

11. The method of claim 8 wherein said second micro-channel comprises a gauge 27 or higher hollow needle comprised of one of stainless steel or glass, or a combination thereof.

12. The method of claim 8 wherein said first and second micro-channels are the same micro-channel.

13. The method of claim 8 wherein said first micro-channel is created using said ultra-short laser pulses.

14. The method of claim 8 further comprising at least two beams of continuous wave, visible spectrum, laser light each of which follows one of said at least two distinct paths travelled by said ultra-short laser pulses.

15. The method of claim 8 wherein said directions of said paths are substantially normal to the surface of the eye at the point of crossing said surface.

16. The method of claim 1 wherein said ultra-short laser pulses have a pulse duration of less than 300 fsec.

17. The method of claim 1 wherein a location of said focal region is determined by automated control of at least one focusing optical lens.

18. The method of claim 1 further comprising the steps of:
observing, by a care-giver, the focal region using an optical microscope; and
automatically adjusting a position of said focal region by adjusting a position of a focusing optical lens determining a location of said focal region by an automated control unit using control feedback obtained via the use of said optical microscope.

* * * * *